United States Patent [19]

Viallet

[11] Patent Number: 5,695,464
[45] Date of Patent: Dec. 9, 1997

[54] METHOD OF INJECTION CONTROLLED BY AN INFUSION PUMP

[75] Inventor: Fabien Viallet, Vence, France

[73] Assignee: Zambon Group SPA, Bresso-Milan, Italy

[21] Appl. No.: 669,297

[22] PCT Filed: Dec. 28, 1994

[86] PCT No.: PCT/FR94/01549

§ 371 Date: Aug. 30, 1996

§ 102(e) Date: Aug. 30, 1996

[87] PCT Pub. No.: WO95/17914

PCT Pub. Date: Jul. 6, 1995

[30] Foreign Application Priority Data

Dec. 29, 1993 [FR] France ............ 93 16022

[51] Int. Cl.[6] ............ A61M 5/00; A61M 5/172
[52] U.S. Cl. ............ 604/67; 604/65; 604/131; 604/151; 604/154; 128/DIG. 1; 128/DIG. 12
[58] Field of Search ............ 604/65–67, 131, 604/151–155, 118, 121, 246, 253, 260; 128/DIG. 1, DIG. 12, DIG. 13; 417/12, 22, 18, 36

[56] References Cited

U.S. PATENT DOCUMENTS

| | | | |
|---|---|---|---|
| 3,623,474 | 11/1971 | Heilman et al. | 604/67 X |
| 3,701,345 | 10/1972 | Heilman et al. | 604/67 |
| 3,858,581 | 1/1975 | Kamen | 604/155 |
| 4,037,598 | 7/1977 | Georgi | 128/DIG. 12 |
| 4,111,198 | 9/1978 | Marx et al. | 604/67 |
| 4,137,913 | 2/1979 | Georgi | 128/DIG. 12 |
| 4,150,672 | 4/1979 | Whitney et al. | 128/DIG. 12 |
| 4,294,248 | 10/1981 | De Fegueiredo | 604/65 X |
| 4,367,435 | 1/1983 | Bailey et al. | 318/280 X |
| 4,396,385 | 8/1983 | Kelly et al. | 604/152 |
| 4,397,639 | 8/1983 | Eschweiler et al. | 604/153 |
| 4,405,318 | 9/1983 | Whitney et al. | 604/155 |
| 4,432,468 | 2/1984 | Siff et al. | 604/65 X |
| 4,468,219 | 8/1984 | George et al. | 604/67 X |
| 4,475,666 | 10/1984 | Bilbrey et al. | 604/152 X |
| 4,498,843 | 2/1985 | Schneider et al. | 604/65 X |
| 4,600,401 | 7/1986 | Kamen | 604/65 |
| 4,731,057 | 3/1988 | Tanaka et al. | 604/153 |
| 4,731,058 | 3/1988 | Doan | 604/155 |
| 4,778,450 | 10/1988 | Kamen | 604/65 |
| 4,838,860 | 6/1989 | Groshong et al. | 604/152 |
| 4,840,620 | 6/1989 | Kobayashi et al. | 604/246 |
| 4,850,805 | 7/1989 | Madsen et al. | 604/153 X |
| 4,898,579 | 2/1990 | Groshong et al. | 604/67 |
| 4,919,596 | 4/1990 | Slate et al. | 604/154 X |
| 4,919,650 | 4/1990 | Feingold et al. | 604/67 |
| 4,985,015 | 1/1991 | Obermann et al. | 604/67 |
| 4,988,337 | 1/1991 | Ito | 604/154 |

(List continued on next page.)

FOREIGN PATENT DOCUMENTS 0 285 403 A3 10/1988 European Pat. Off. .
0 039 044 A1 11/1991 European Pat. Off. .

*Primary Examiner*—Sam Rimell
*Assistant Examiner*—Robert V. Racunas
*Attorney, Agent, or Firm*—E. C. Hancock; F. A. Sirr; Holland & Hart llp

[57] ABSTRACT

Method for the controlled injection of a liquid in a tube by means of a peristaltic type pump actuated by a rotary d.c. motor (12) controlled by a control unit (10) such as a microprocessor, wherein an optical encoder (18) sends pulses to said control unit (10) during the intermittent operation of the motor. The method comprises operating the motor for period corresponding to a number of pulses equal to a set value. For each operating phase of the motor (12), equal to a predetermined number of pulses, the set value is reduced by the number of pulses transmitted during the preceding deceleration phase when the power supply is interrupted. The resulting error in the level of the volume of liquid to be injected thus remains approximately constant for the entire length of the injection period. The method according to the invention may be advantageously used in a programmable portable infusion system.

11 Claims, 2 Drawing Sheets

U.S. PATENT DOCUMENTS

| | | | |
|---|---|---|---|
| 5,181,910 | 1/1993 | Scanlon | 604/67 |
| 5,219,330 | 6/1993 | Bollish et al. | 604/131 X |
| 5,256,157 | 10/1993 | Samiotes et al. | 604/246 |
| 5,318,521 | 6/1994 | Slettenmark | 604/67 |
| 5,320,503 | 6/1994 | Davis | 604/153 X |
| 5,389,078 | 2/1995 | Zalesky et al. | 604/151 |
| 5,425,716 | 6/1995 | Kawasaki et al. | 604/152 |
| 5,442,267 | 8/1995 | Harada | 318/280 |
| 5,463,293 | 10/1995 | Matsui | 318/280 X |
| 5,534,691 | 7/1996 | Holdaway et al. | 604/67 X |
| 5,584,667 | 12/1996 | Davis | 417/53 |
| 5,609,576 | 3/1997 | Voss et al. | 604/67 |

METHOD OF INJECTION CONTROLLED BY AN INFUSION PUMP

TECHNICAL FIELD

The present invention involves a procedure for the controlled injection of liquid in a tube used in a system of the type comprising a source of liquid to be injected connected by way of an upstream part of the tube to a pump which acts by means of pressure exerted on the tube so as to inject the liquid deriving from the source of the liquid towards a downstream part of the tube, a rotary motor under continuous current to actuate the pump and obtain a quantity of liquid injected as a function of the angle at which the motor rotates, and a motor control unit, with the motor transmitting to the control unit pulses, the frequency of which is proportional to the angle through which the motor rotates.

STATE OF THE TECHNIQUE

More and more human diseases are treated using the injection of a medicamentous substance into the patient's body. Thus, in the treatment of diabetes, it is necessary to carry out regular injections of insulin to the patients. Other diseases such as cancer are also treated by means of the injection of medicamentous substances. However, regular injection via needle and syringe present numerous problems, such as the regularity with which the injections must be respected, and especially the problem raised by the cutaneous damage caused by the multiple injections given.

The solution was thus for the patient to have a continuous treatment using an infusion needle permanently positioned through the entry of the catheter implanted in the patient, usually by means of an implanted chamber connected to a pump.

The improvement provided by this technique was that the patient wore the pump on his person in a pocket, or attached to a belt. The pump, actuated by an electric motor, injects, in a continuous manner, the medicamentous substance into the catheter, and thus provides the chemotherapy necessary to the patient without having to carry out continual injections via needle and syringe.

Regardless of the mechanical system used by pumps for the injection of a medicamentous substance (peristaltic, nutation, fingers, cams . . . ), a continuous injection means a fragmentation of the volume to be delivered in small quantities, injected at regular intervals. This fragmentation technique is necessary, since the volumes injected are small for generally long durations, especially when it involves ambulatory and portable systems. In order to get close to continuous functioning, the process is always the same: the pump injects into the tube connected to the infusion needle a quantity of medicamentous substance called bolus, which is always identical, for example, 25 ul or 50 ul. Only the period of fragmentation may be modified so as to obtain a treatment over a longer or shorter period.

The above method has the advantage of requiring a relatively simple motor control management. However, it has the disadvantage that pharmacokinetic results are not always adapted to the treatment. In effect, since the minimal bolus is fixed, a small volume injection (50, 100 ml) of medicamentous substance having to be given over a long duration (4 or 5 days) necessarily requires long fragmentation periods. Thus, if the treatment requires an injection of 100 ml for 5 days, the theoretical flow is 0.83 ml/h or 13.88 ul/mn. However, since the system supplies a bolus of 50 ul, a period of 3 mn 36 sec is necessary, that is, the system will deliver 50 ul every 3 mn 36 sec.

This kind of control does not provide good results from the pharmaco-kinetic point of view, since the infusion leads to a considerable fluctuation in the concentration of the product injected between two injections, as is illustrated in FIG. 1. With each injection represented on the first graphic by pulses separated in time by a fragmentation period, the concentration of the medicamentous substance injected into the patient's organism increases up to a maximal concentration, Cmax. Subsequent to this injection and until the following injection, the concentration decreases to a minimal concentration, Cmin.

In order to decrease maximally the Cmax/Cmin ratio, it is necessary to provide injections as close together as is possible, and this requires the injection of smaller elementary boli, as well as a shorter fragmentation period. This can only be carried out using mechanical systems, of the "continuous kind", equipped with an elaborate control motor so as to obtain acceptable precision. As a function of the flows required, it is necessary to be able to vary the two parameters of bolus and fragmentation period, or only the bolus, if the period chosen is acceptable in all cases.

However, this type of control requires great precision at the time of each injection, which leads to the necessity of having available cumbersome equipment and complicated software (of the PID type), for control in position and/or in speed. Moreover, the equipment, by virtue of its being heavy and cumbersome, and the software, by virtue of its taking up much CPU time, are both large consumers of energy, and this is absolutely not adapted to ambulatory pumps which are not equipped with batteries for supplying the unit.

SUMMARY OF THE INVENTION

An initial aim of the invention is thus to provide a procedure for the injection of liquid in a tube which allows a distribution of the liquid which is patently homogeneous, with time, to be obtained.

Another aim of the invention is to provide a procedure which allows the control and regulation of the injection of liquid in a tube, using, at each period, a correction based partially on the quantity of liquid injected during the preceding period.

Yet another aim of the invention is to create a procedure for the injection of a medicamentous substance by means of an ambulatory pump which permits a ratio between the maximal concentration and minimal concentration of the substance in the patient's organism which is very close to one.

The object of the invention is thus a procedure characterised by the following stages, put to work each time the motor is started up: count the pulses transmitted by the motor and provide a signal of motor supply break when the number of pulses reaches a warning value of m, count the pulses transmitted by the motor between the supply break and its outage, add m+n and add to the total sum of pulses accumulated since the first motor start-up, subtract from this thus found sum a theoretical value equal to the product of a predetermined number by N, in order to obtain an algebraic error, and replace the warning value by a new value equal to the difference between the said predetermined number and a number equal to the sum of the algebraic error and a predetermined constant so that the algebraic error is approximately the same at each phase of motor functioning. In the preferred performance mode of the invention, the predetermined constant is defined as being the mean number .of pulses transmitted by the motor between the supply break and outage when the total number of pulses transmitted by the motor is equal to the said predetermined number.

BRIEF DESCRIPTION OF THE DRAWINGS

The aims, objects and characteristics of the invention will be better understood upon reading the description which follows, made with reference to the drawings, in which.

DETAILED DESCRIPTION OF THE INVENTION

Figure 1:
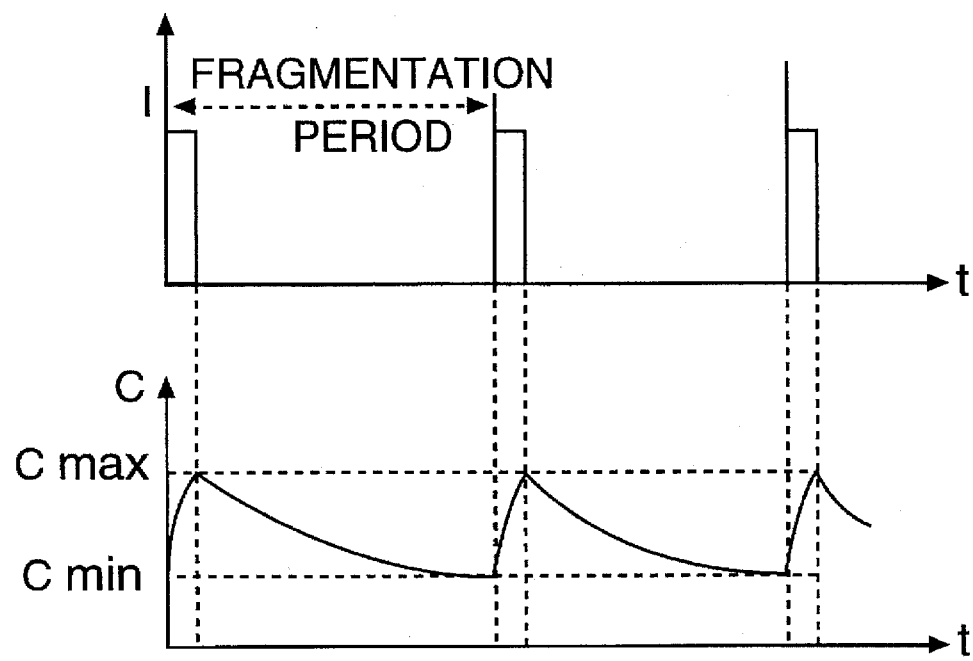
FIG. 1 represents the diagrams in relation to the times of pulses of injection of a medicamentous substance and of the resulting concentration of substance in the patient's organism.

As mentioned previously, one of the aims of the invention is to obtain a ratio of maximal and minimal concentrations (see FIG. 1) of the medicamentous substance in the patient's organism, one that will be closest to 1.

Figure 2:
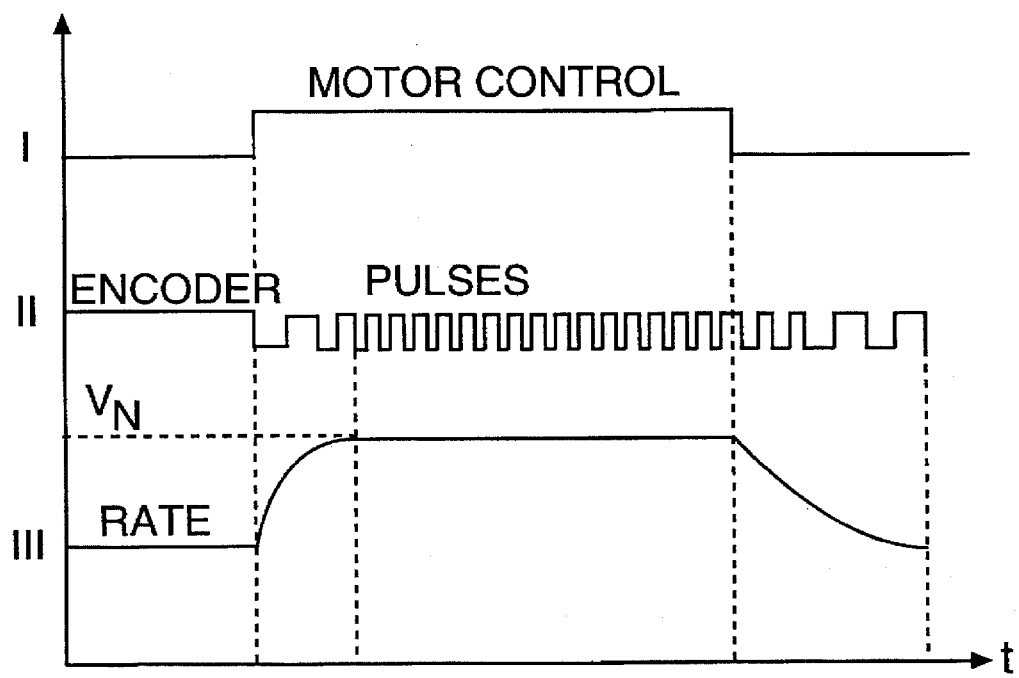
FIG. 2 represents, on a same diagram in relation to the time, the curves of the control motor, the pulses transmitted back by the motor, and motor speed.

In order to achieve this result it is, a priori, useful to understand the functioning of a continuous current motor used for the control of the pump referenced in FIG. 2. Generally speaking, when the motor is in the phase of functioning represented by curve 1, it transmits coder pulses to the control unit.

As illustrated in curve III, when the motor is started up it accelerates until reaching its nominal speed, Vn, after a given time. It then remains at this nominal speed until supply is ceased. As of this cut-off, it decelerates until outage is complete. There is thus pulse transmission by the motor during the entire duration in which it is controlled, but also during its deceleration phase after supply break. In order to prevent the concentration of the medicamentous substance from getting too low, logic indicates that the fragmentation period must be decreased (see FIG. 1), at the same time that the quantity of medicamentous substance injected at each start-up of the motor also must be decreased. However, as has just been seen, referenced in FIG. 2, the motor presents a deceleration phase after the end of motor control, during which time the pump continues to inject the medicament, and this is impossible to know precisely, unless very sophisticated means are available, as has already been mentioned, and which are incompatible with a portable pump. The more one decreases the fragmentation period, the more one increases the frequency of motor start-up and the more one increases the precision error on the quantity injected due to the motor's deceleration phases.

The principle of the invention thus consists in controlling the duration of motor functioning upon each start-up, so as to compensate for the error previously accumulated, and this by virtue of the transmission of pulses (generated by an optical or magnetic coder) by the motor towards the control unit.

Firstly, determination of a short fragmentation period which prevents the concentration of the medicamentous substance from descending too low must be made. Generally speaking, it is necessary to choose this period well below the half-life of the substance injected. Knowing the total volume to be injected, the basal volume or bolus to be injected at each period is determined. This basal volume is easily converted into the number of pulses of the coder, since the volume delivered by each rotation of the motor, and thus the volume injected upon each pulse, is known. Thus, the number of theoretical pulses corresponding to motor functioning for each period of fragmentation is known. The procedure will therefore consist in rectifying, at the time of each motor start-up, the number of theoretical pulses of the control motor via the absolute error of the accumulated number of pulses, an error due to the period of motor deceleration, of which it is impossible to determine the duration with precision, in order to obtain a warning value (in number of pulses) of the motor control.

The following example will permit a better understanding of the principle of the invention. Supposing that the fragmentation period chosen for the treatment had permitted a determination of a theoretical number of 10 pulses, during which the motor must be controlled at each phase, N, of functioning, the values of the different variables (warning value, relative error, absolute error . . . ) during the phases of functioning are shown in table I.

| Phase of functioning (n) | 1 | 2 | 3 | 4 | 5 | 6 | 7 | 8 |
|---|---|---|---|---|---|---|---|---|
| warning value (Vn) | 10 | 4 | 7 | 6 | 6 | 7 | 6 | 6 |
| phase number of pulses (Mn) | 16 | 7 | 11 | 10 | 9 | 11 | 10 | 10 |
| relative error (en) | 6 | 3 | 4 | 4 | 3 | 4 | 4 | 4 |
| accumulated number of pulses (Nn) | 16 | 23 | 34 | 44 | 53 | 64 | 74 | 84 |
| absolute error (En) | 6 | 3 | 4 | 4 | 3 | 4 | 4 | 4 |

At each phase of functioning, the warning value is equal to 10 (theoretical number of the motor control), decreased by the error on the total number of pulses desired in order to respect chronotherapy. Thus, at phase 2, the error is 6 and therefore the warning value is 4. At phase 3, the error is 3, and the warning value is established at 7 . . . and so on. It is seen upon reading the table above that the accumulated error tends to stabilise at 4, or, more generally, between 3 and 5. Such an error corresponds, at the end of the treatment, to several hundreds of nanolitres, and thus is negligeable when compared to the 50 or 100 ml injected in toto. It should be noted that this error is directly linked to the moment of motor inertia, thus to the speed reached by the motor at the time of supply break from the motor.

Upon reading the figures in the example given below it is seen that the absolute error is in fact equal to the relative error (number of pulses sent by the motor during the deceleration phase).

This is due to the fact that:

if Nn is the number of pulses accumulated in phase n,

Vn is the warning value and en is the relative error in phase n, the number of accumulated pulses in phase n is equal to:

$$N_n = N_{n-1} + V_n + e_n$$

and thus the absolute error in phase n is equal to $$E_n = N_n - (10)(n)$$

that is, $$E_n = N_{n-1} + V_n + e_n - (10)(n)$$

and as at each phase the new wanting value is calculated by subtracting from 10 the preceding absolute error, that is:

$$V_n = 10 - [N_{n-1} - (10)(N-1)]$$

from which the conclusion is $$E_n = e_n$$

Thus, at each phase the absolute error is equal to the relative error, that is, to the number of pulses in the motor's deceleration phase.

As has been previously mentioned, the number of pulses sent by the motor is not a value which can be determined with certainty. It is nonetheless possible to know the approximate value. For this reason, the procedure which has just been described can be improved by introducing a corrective value, predetermined in the calculation of the warning value. The warning value is, at each phase, equal to the theoretical number of pulses decreased from the preceding absolute error to which is added a predetermined constant permitting a total number of pulses to be obtained (Y comprises the deceleration phase)), approximately equal to the theoretical number. Thus, still within the hypothesis of a theoretical value of 10 pulses at each phase of functioning and considering a corrective constant of 4, the values of the different variables (warning value, relative error, absolute error . . . ) during the functioning phases are shown in table II which follows.

| Phase of functioning (n) | 1 | 2 | 3 | 4 | 5 | 6 | 7 | 8 |
|---|---|---|---|---|---|---|---|---|
| warning value (Va) | 6 | 6 | 5 | 7 | 6 | 6 | 5 | 7 |
| Phase number of pulses | 10 | 11 | 8 | 11 | 10 | 11 | 8 | 11 |
| relative error (en) | 4 | 5 | 3 | 4 | 4 | 5 | 3 | 4 |
| number accumulated of pulses (Nn) | 10 | 21 | 29 | 40 | 50 | 61 | 69 | 80 |
| absolute error (En) | 0 | 1 | −1 | 0 | 0 | 1 | −1 | 0 |

Here again, it is interesting to calculate the absolute error in order to note that it is directly deducted from the relative error.

If Nn is the number of accumulated pulses in phase n, Vn is the warning value and en is the relative error relating to phase n; the number of accumulated pulses at phase n is equal to:

$$N_n = N_n + V_n + e_n$$

and thus the absolute error at phase n is equal to:

$$E_n = N_n - (10)(n)$$

that is $$E_n = N_{n-1} + V_n + e_n - (10)(n)$$

and as at each phase the new warning value $V_n$ is calculated by subtracting from 10 the previously increased warning value $V_n$ decreased by the above mentioned corrective constant, 4 which equals, that is:

$$V_n = 10 - [N_{n-1} - 10 \cdot (n-1)] - 4$$

$$V_n = 10 \cdot n - N_{n-1} - 4$$

Concluding that:

$$E_n = e_{n-4}$$

One thus notes that it again suffices to consider the relative error of the preceding phase in order to calculate the warning value for each phase, except for the initial phase where the warning value is equal to the number of theoretical pulses decreased from the predetermined constant.

In order to improve the procedure, one may envisage having several motor supply voltages which can be selected, permitting a broader range of use. In effect, the lower the pressure is, the less the error is marked, due to a lower nominal speed.

In the invention's preferred performance mode, the continuous current motor supplies, under 5V controls, the pump with a reduction of 1/27, and an optical coder supplying 16 pulses per motor rotation.

With the characteristics of the pump, such as the quantity of liquid injected at each rotation of the pump, that is, 25 ul, the quantity injected at each pulse is 25 ul/27×16=57.87 nl.

If a fragmentation period of 5s is chosen, that is, if the motor is started up every 5s, and taking a theoretical number of pulses which is equal to 10 at each phase of operation, the quantity of medicamentous substance injected per hour will be:

57.87 nl×10×720=416.66 ul

With the same pump, but by chosing a theoretical number of pulses which is equal to 20, an hourly quantity of 883.32 ul is obtained. Thus, with a same fragmentation period, but by choosing a different theoretical number of pulses, it is possible to adapt the chronotherapy depending on the kind of treatment desired.

Figure 3:
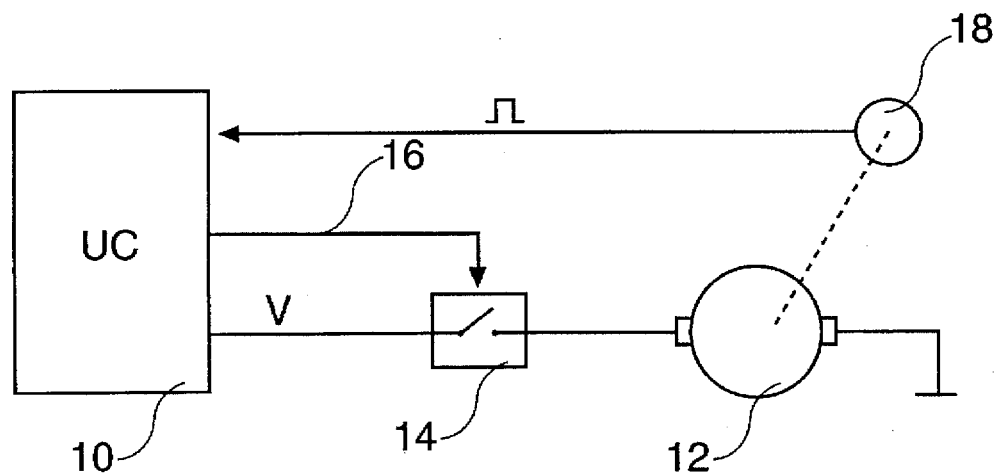
FIG. 3 schematically represents an initial means of creating the invention using a microcontroller, and FIG. 4 schematically represents a second means of creating the invention using a microprocessor.

The invention procedure can be implemented in a general manner by means of the system illustrated in FIG. 3. The control unit is a micro-controller providing supply V to motor 12 via switch 14. The micro-controller keeps in the memory the value of the theoretical number of pulses $V_n$ to be delivered to each phase of motor operation. At the start-up of an operational phase, the microcontroller sends a validation signal to line 16 to close switch 14 and supply motor 12. The coder, 18, transmits pulses $M_n$ back to the micro-controller 10. The former are discounted from the warning value up to value O. At this value, the microcontroller stops transmitting the validation signal on line 16, and the motor, 12, is no longer supplied. During the deceleration phase, the pulses transmitted by coder 18 are counted in order to determine the relative error $e_n$ which will serve to calculate the absolute error $E_n$ and the new warning value $V_n$ to be applied at the time of the following phase of operation.

Figure 4:
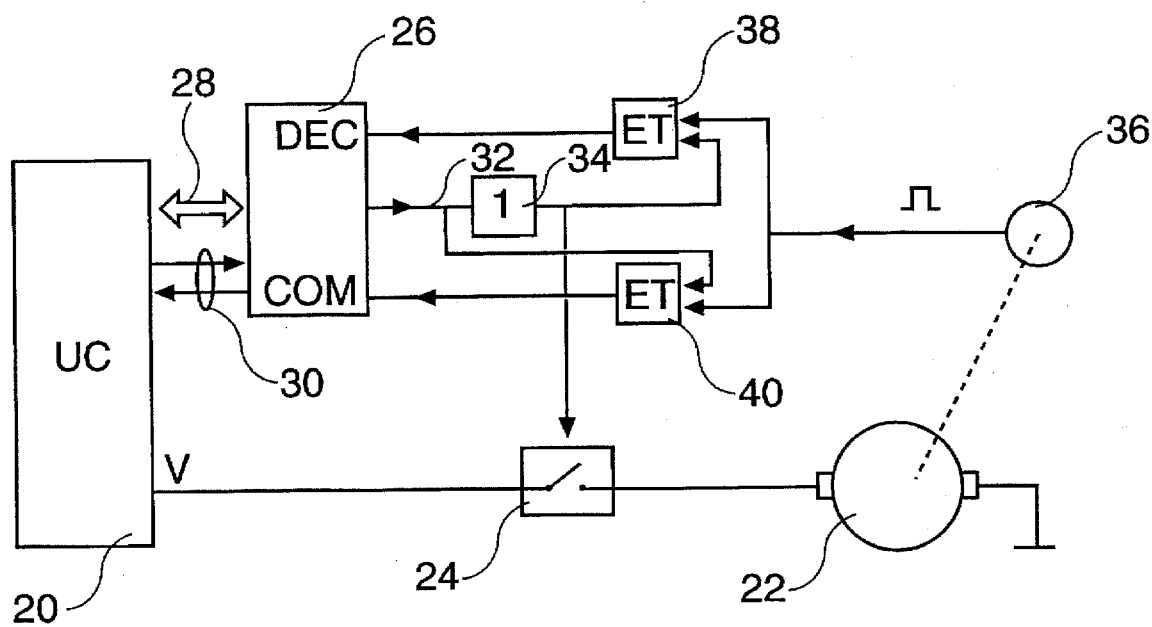

The invention's preferred performance mode can be carried out by the system illustrated in FIG. 4. In this concept, the control unit is simply a microprocessor 20. As previously, the supply voltage is supplied to motor 22 via the intermediary of a switch, 24. A counter/discounter (+/− measurement control), 26, receives from/or transmits its data to the microprocessor, 20, by means of an 8 byte bus, 28, with reading control of decoding taking place by means of the control lines, 30. At the start-up of a phase of motor functioning, the warning value $V_n$ equal to a decreased theoretical number of pulses of a predetermined corrective constant is loaded into the counter/discounter (+/− measurement control) 26. The exit, 32, of the latter is actuated only when the counter is empty and thus is at 0, and 1 is supplied at the exit of the inverter, 34, which has the effect of closing the switch, 24, allowing supply to the motor, 22. Consequently, the coder, 36, transmits pulses. By virtue of the fact that the exit of the inverter, 34, is at 1, gateway ET5 38 allows passage, whilst gateway ET 40, receiving 0 at the exit of line 32 is blocked. The pulses transmitted by coder 36 are thus supplied, via circuit ET 38 at the entry of DEC counting of the counter/discounter (+/− measurement control) 26. When the counter/discounter (+/− measurement control) 26 reaches value 0, a signal, 1, is sent to line 32, which renders gateway ET 40 passable, but blocks gateway ET 38 by virtue of the fact that the exit of inverter 34 opens switch 24 and cuts the supply of motor 22. The pulses provided by coder 36 during the motor's deceleration phase are thus transmitted, via gateway ET 40, to the entry of COM counting of the counter/discounter (+/− measurement control) 26. At the end of the deceleration phase, the value reached by counter 26 read by microprocessor 20, by means of bus 28, is subtracted from the theoretical number of pulses (10 in the examples given above, so as to obtain the new warning value to be loaded onto the counter/discounter (+/– measurement control) 26 at the start-up of the following phase.

The software necessary to implement the invention procedure in the system illustrated in FIG. 4 is very simple. In effect, one begins by providing the system constants, that is:

the volume injected by motor rotation the number of pulses per motor rotation

From these constants the software easily determines, as a function of the treatment duration and the total volume to be delivered during the treatment, the number of pulses to be generated at each period or warning value, that is:

NPP: number of pulses per period

The software is then simply made up of the following instructions, carried out at each phase of motor operation:

reading of the counter→ERR reset of counter at zero calculation of NPP–ERR=VAL (warning value)

Loading of VAL into the discounter (–measurement control)

If the warning value is decreased in the initial phase by a corrective value with a view to decreasing the error value as has been mentioned previously, it is necessary to establish the flow value of the variable NPP not equal to the number of pulses to be obtained per period, but to this decreased number of the corrective value.

In order to improve the procedure established by the system illustrated in FIG. 4, it is possible to join to it a self-adaptating software. In effect, due to the fact that the parameters may be different depending on the application (large flow, small flow . . . ) and that the components used (silicone tube, motor, reduction ratio . . . ) may be different, a motor response represented by a number of pulses following supply break which is different depending on the cases is obtained.

The self-adaptation software comprises firstly a learning sequence during which the number of pulses generated following supply break of the motor or the progressive warning values is determined.

| Warning value | Number of pulses during deceleration |
|---|---|
| 1 pulse | n1 |
| 10 pulses | n10 |
| 50 pulses | n50 |
| 100 pulses | n100 |
| 200 pulses | n200 |
| 500 pulses | n500 |

The value ni is determined by a number, i, of pulses sufficient for the motor to reach its nominal speed. The number of maximal pulses may be 200, 500 or even 1000.

Subsequently, starting with values n1, n10, n50 . . . the software makes a linear interpolation for each pair of 2 successive warning values in order to determine a number, n, for any warning value whatsoever.

The values, ni, which were thus determined are used during an infusion in order to determine the constant to be subtracted from the theoretical warning value so as arrive at the real warning value to be applied at each phase of motor operation.

However, a third phase of software self-adaptation may also be foreseen and it consists in establishing a table in which the warning value to be applied by subtracting from the theoretical warning value the number of corresponding pulses obtained during the learning sequence of the software is determined. Thus, the table obtained will contain the relative error value to be applied for each theoretical warning value, as it appears in table II above.

Although in the preferred performance mode the invention's procedure is partially implemented using software (in the microprocessor in FIG. 4) and partially via the equipment, it is in the hands of the professional to implement this procedure using only logical circuits. However, given the progress in making semiconducting devices miniature, it is more prudent to use the power of a microprocessor to carry out some functions with the help of software.

I claim:

1. A method for injecting a relatively large quantity of a liquid into a tube of an injection system, said injection system having:

a source of said liquid;

a pump connected to said source of liquid and to said tube for supplying liquid under pressure to said tube and thereby injecting said liquid from said source of liquid into said tube;

an energizable rotary motor connected to actuate said pump;

a coder connected to said motor and providing a serial pulse output that is responsive to an angle through which said motor rotates;

said motor operating to inject said relatively large quantity of liquid into said tube by way of a summation of a plurality of relatively small quantities of said liquid that are injected into said tube as a result of a like plurality of energization phases of said motor;

each of said plurality of motor energization phases comprising, a motor acceleration interval that is responsive to energization of said motor by said control unit;

a motor nominal speed interval that follows said motor acceleration interval and is responsive to continued energization of said motor by said control unit; and a motor deceleration interval that follows said motor nominal speed interval and that is responsive to deenergization of said motor by said control unit, each of said relatively small quantities of said liquid being a function of an angle through which said pump rotates during a said energization phase that comprises a said acceleration interval, a said nominal speed interval, and a said deceleration interval;

said method comprising the steps of, providing an initial pulse warning value;

energizing said motor;

counting first pulses within said serial pulse output of said coder during a time interval of motor energization by said step of energizing said motor;

comparing said counted pulses to said initial pulse warning value;

deenergizing said motor when said counted first pulses are equal in number to said initial pulse warning value;

counting second pulses within said serial pulse output of said coder during a time interval during which said motor decelerates after said motor deenergization step;

forming a new pulse warning value that is equal to said initial pulse warning value less said counted second pulses;

using said new pulse warning value as a new initial pulse warning value; and repeating said method steps.

2. The method of claim 1:

wherein said motor is a DC motor; and wherein said motor control unit output comprises a DC voltage of a fixed magnitude.

3. The method of claim 1 including the step of:

repeating said method steps a plurality of times;

determined when a summation of a like plurality of relatively small quantities of said liquid equals said relatively large quantity of said liquid; and stopping said method.

4. The method of claim 3:

wherein said motor is a DC motor; and wherein said motor control unit output comprises a DC voltage of a fixed magnitude.

5. The method of claim 1 including the steps of:

summing said serial pulse output of said coder for a plurality of repetitions of said method steps;

determining when said summation of said serial pulse output of said coder indicates that said plurality of repetitions of said method steps has operated to produce a summation of a like plurality of relatively small quantities of said liquid wherein said summation equals said relatively large quantity of said liquid; and stopping said method as a result of said determining step.

6. The method of claim 5:

wherein said motor is a DC motor; and wherein said motor control unit output comprises a DC voltage of a fixed magnitude.

7. A method of injecting a desired quantity of liquid into a tube from a liquid source by the use a pump that is located intermediate said liquid source and an end of said tube, said method comprising:

providing a DC rotary motor connected to actuate said pump;

providing a coder connected to be operated by rotation of said motor, said coder providing a pulse output that contains one coder pulse for one unit of motor rotation;

providing a motor control unit having a DC output connected to energize said motor and having an input connected to receive said pulse output;

providing as a result of one energization phase of said motor by said motor control unit DC output, (1) a motor acceleration interval that is responsive to initial energization of said motor by said control unit DC output, (2) a motor speed interval that immediately follows said motor acceleration interval, and (3) a motor deceleration interval that immediately follows said motor speed interval and is responsive to deenergization of said motor by said control unit DC output;

providing an initial pulse warning value to said motor control unit;

energizing said motor with said control unit DC output;

counting a first number of pulses during a motor acceleration/energization interval that results from said step of energizing said motor;

comparing said first number of pulses to said initial pulse warning value;

deenergizing said motor when said comparing step indicates that said first number of pulses equals said initial pulse warning value;

counting a second number of pulses during a motor deceleration interval that results from said motor deenergizing step;

forming a next pulse warning value by subtraction said second number of pulses from said initial pulse warning value;

using said next pulse warning value as said initial pulse warning value; and repeating said method steps.

8. The method of claim 7 including the step of:

repeating said method steps a plurality of times;

determining when said repetition of said method for said plurality of times results in injection of said desired quantity of said liquid into said tube; and ceasing to repeat said method as a result of said determining step.

9. The method of claim 8 including the steps of:

providing said control unit DC output as a substantially constant magnitude DC output; and providing said a motor speed interval as a substantially constant motor speed interval.

10. In an infusion system for use in injecting a medicamentous substance into a catherer that is implanted within a patient's body, said system having a pump acting to apply pressure to a tube that is connected between a medicamentous substance reservoir and said catheter, a DC motor connected to said pump to actuate said pump in accordance with rotation of said DC motor, and a coder associated with said DC motor to provide one output pulse for each unit of DC motor rotation, a method of injecting a fixed quantity of said medicamentous substance into said catherer, comprising the steps of:

providing an up/down counter;

providing an initial phase pulse warning value;

loading said initial phase pulse warning value into said up/down counter;

energizing said DC motor with a DC voltage;

decrementing said up/down counter using said coder output pulses;

determining when said up/down counter contains a zero count;

deenergizing said DC motor as a result of said determining step;

incrementing said up/down counter from said count of zero using said coder output pulses until the end of a deceleration interval of said DC motor that results from said deenergizing step;

at said end of said deceleration interval, determining a deceleration count within said up/down counter;

subtracting said deceleration count from said initial phase pulse warning value in order to form a next phase pulse warning value;

loading said next phase pulse warning value into said up/down counter;

repeating said method a number of times until it is determined that said fixed quantity of said medicamentous substance has been injected into said catherer; and ceasing to repeat said method when it is determined that said fixed quantity of said medicamentous substance has been injected into said catherer.

11. The method of claim 10 including the step of:

energizing said DC motor with a substantially constant magnitude DC voltage, to thereby provide a motor acceleration interval that is followed by an interval of substantially constant speed of rotation of said DC motor.

* * * * *